United States Patent [19]

Umezawa et al.

[11] 4,140,849

[45] Feb. 20, 1979

[54] KANAMYCIN C DERIVATIVES

[75] Inventors: Hamao Umezawa, Tokyo; Shinichi Kondo, Yokohama, both of Japan

[73] Assignee: Zaidan Hojin Biseibutsu Kagaku Kenkyu Kai, Tokyo, Japan

[21] Appl. No.: 834,753

[22] Filed: Sep. 19, 1977

Related U.S. Application Data

[63] Continuation-in-part of Ser. No. 799,806, May 23, 1977.

[51] Int. Cl.$^2$ ............................................. C07H 15/22
[52] U.S. Cl. ...................................... 536/10; 424/180; 536/17
[58] Field of Search ........................................... 536/10

[56] References Cited

U.S. PATENT DOCUMENTS 3,781,268  12/1973  Kawaguchi et al. .................. 536/10
3,939,143  2/1976   Umezawa et al. .................... 536/10
4,001,208  1/1977   Umezawa et al. .................... 536/10
4,029,882  6/1977   Wright ................................. 536/10

OTHER PUBLICATIONS

Fugisawa et al. "The Jour. Of Antibiotics", vol. XXVII, No. 9, 1974, pp. 677–681.

Primary Examiner—Johnnie R. Brown
Attorney, Agent, or Firm—Herbert W. Taylor, Jr.

[57] ABSTRACT

1-N-(L-4-amino-2-hydroxybutyryl) derivatives of kanamycin C, 3'-deoxykanamycin C and 3',4'-dideoxykanamycin C have been prepared which possess high antibacterial activity against a wide variety of drug-resistant bacteria. These new derivatives are prepared by reacting L-4-amino-2-hydroxybutyric acid or a functional equivalent thereof with the 1-amino group of kanamycin C, 3'-deoxykanamycin C or 3',4'-dideoxykanamycin C.

4 Claims, No Drawings

KANAMYCIN C DERIVATIVES

CROSS-REFERENCE TO RELATED APPLICATION

This application is a continuation-in-part of our prior, copending application Ser. No. 799,806 filed May 23, 1977.

BACKGROUND OF THE INVENTION

1. Field of the Invention

This invention relates to new kanamycin C derivatives active against a wide variety of kanamycin-resistant bacteria, and a process for the preparation of these new kanamycin C derivatives. More particularly, this invention relates to new and useful 1-N-(L-4-amino-2-hydroxybutyryl) derivatives of kanamycin C, 3'-deoxykanamycin C and 3',4'-dideoxykanamcyin C, and the preparation thereof.

2. Description of the Prior Art

Butirosin B, that is, 1-N-(L-4-amino-2-hydroxybutyryl)-ribostamycin may be produced by a fermentative method ("Tetrahedron Letters" 28, 2617–2620 (1971)), and 1-N-(L-4-amino-2-hydroxybutyryl) derivatives of kanamycin A and kanamycin B are synthesized (U.S. Pat. No. 3,781,268 (1973)). 1-N-(L-4-amino-2-hydroxybutyryl) derivatives of other some aminoglycosidic antibiotics are also synthesized (U.K. Pat. No. 1,426,908 (published in Mar. 1976)). Furthermore, deoxy derivatives of kanamycins are also synthesized on the basis of the previous findings which were obtained by H. Umezawa et al. with respect to the mechanism of resistance of bacteria to aminoglycosidic antibiotics owing to various inactivating enzymes produced by the resistant bacteria. For instance, 3',4'-dideoxykanamycin B and 3'-deoxykanamycin B are synthesized which are active against the resistant bacteria producing aminoglycoside 3'-phosphotransferase (U.S. Pat. Nos. 3,753,973 and 3,929,762; and H. Umezawa's "Advances in Carbohydrate Chemistry and Biochemistry" 30, 183 (1974) and "Drug Action and Drug Resistance in Bacteria" 2, 211 (1975)). 3',4'-Dideoxykanamycin B has been used widely in therapeutic treatment of infections caused by a variety of the resistant bacteria, including *Pseudomonas aeruginosa*. However, it has been found that these deoxy derivatives of kanamycin B do not inhibit the growth of such resistant bacteria which are capable of producing the aminoglycoside 6'-acetyltransferase and 2''-nucleotidyltransferase. As a result of a further research, we have succeeded in synthetically converting the 6'-amino group of kanamycin B or its deoxy derivatives into hydroxyl group and thereby producing kanamycin C and its deoxy derivatives which inherently cannot be inactivated by the 6'-acetyltransferase (see co-pending U.K. Patent Application No. 12266/77 and co-pending U.S. Pat. Application Ser. No. 799,806). However, kanamycin C, 3'-deoxykanamycin C and 3',4'-dideoxykanamycin C so obtained are not able to inhibit the growth of such resistant bacteria producing the 2''-nucleotidyltransferase.

SUMMARY OF THE INVENTION

In these circumstances, we have made further research, and as a result we have succeeded in synthesizing new compounds, 1-N-(L-4-amino-2-hydroxybutyryl) derivatives of kanamycin C, 3'-deoxykanamycin C and 3',4'-dideoxykanamycin C which are active against a wide variety of aminoglycoside-resistant bacteria, including the 2''-nucleotidyltransferase-producing bacteria.

Thus, an object of this invention is to provide such new kanamycin C derivatives which inherently cannot be inactivated by the 3'-phosphotransferase extensively distributed in a variety of the aminoglycoside-resistant bacteria and also cannot be inactivated by the 6'-acetyltransferase and the 2''-nucleotidyltransferase, which is accordingly active against not only the aminoglycoside-resistant bacteria producing the 3'-phosphotransferase, but also the aminoglycoside-resistant bacteria producing the 6'-acetyltransferase and the aminoglycoside-resistant bacteria producing the 2''-nucleotidyltransferase and which exhibits a very much low toxicity. Another object of this invention is to provide a new process for the preparation of such new kanamycin C derivatives which can be operated in a facile way and with a reasonable efficiency. Another objects will be seen from the following descriptions.

DETAILED DESCRIPTION OF THE INVENTION

According to a first aspect of this invention, there is provided the novel 1-N-(L-4-amino-2-hydroxybutyryl) derivatives of kanamycin C, 3'-deoxykanamycin C or 3',4'-dideoxykanamycin C represented by the general formula:

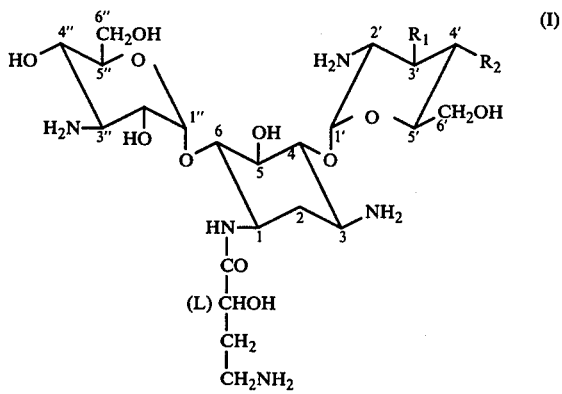

wherein $R_1$ and $R_2$ are each hydroxyl, or $R_1$ is hydrogen and $R_2$ is hydroxyl or $R_1$ and $R_2$ are each hydrogen or a nontoxic, pharmaceutically acceptable acid-addition salt thereof.

The new compounds according to this invention include 1-N-(L-4-amino-2-hydroxybutyryl)-kanamycin C [the compound of the formula (I) where both $R_1$ and $R_2$ are hydroxyl group]; 1-N-(L-4-amino-2-hydroxybutyryl)-3'-deoxykanamycin C [the compound of the formula (I) where $R_1$ is hydrogen atom and $R_2$ is hydroxyl]; and 1-N-(L-4-amino-2-hydroxybutyryl)-3',4'-dideoxykanamycin C [the compound of the formula (I) where both $R_1$ and $R_2$ are hydrogen atom] as well as pharmaceutically acceptable nontoxic acid-addition salts thereof. The chemical, physical and biological properties of these new compounds are as follows:

1-N-(L-4-Amino-2-hydroxybutyryl)-kanamycin C is a substance in the form of a colorless powder having no definite melting point but decomposing at 167–180° C. It shows a specific optical rotation $[\alpha]_D^{26}$ +91° (c 1, water). Its elemental analysis is coincident with the theoretical values of $C_{22}H_{43}N_5O_{13} \cdot H_2O$ (C 43.77%, H 7.51%, N 11.60%). This substance gives a single spot positive to ninhydrin at Rf. 0.18 in thin layer chromatography on silica gel (available under a trade name "ART 5721", a product of Merck Co., Germany) developed with butanol-ethanol-chloroform-17% aqueous ammonia (4:5:2:8 by volume) and at Rf 0.19 in the same thin layer chromatography developed with chloroform-methanol-28% aqueous ammonia (1:4:2 by volume) as the development solvent, respectively.

1-N-(L-4-Amino-2-hydroxybutyryl)-3'-deoxykanamycin C is a substance in the form of a colorless powder having no definite melting point but decomposing at 151°–160° C. It shows a specific optical rotation $[\alpha]_D^{27}$ +83° (c 1, water). Its elemental analysis is coincident with the theoretical values of $C_{22}H_{43}N_5O_{12} \cdot H_2O$ (C 44.96%, H 7.72%, N 11.92%). This substance gives a single spot positive to ninhydrin at Rf 0.22 in the above-mentioned silica gel thin layer chromatography developed with the first-mentioned development solvent and at Rf 0.24 in the same thin layer chromatography developed with the second-mentioned development solvent, respectively.

1-N-(L-4-Amino-2-hydroxybutyryl)-3',4'-dideoxykanamycin C is a substance also in the form of a colorless powder having no definite melting point but decomposing at 142°–158° C. It shows a specific optical rotation $[\alpha]_D^{28}$ +76° (c 1, water). Its elemental analysis is coincident with the theoretical values of $C_{22}H_{43}N_5O_{11} \cdot H_2O$ (C 46.22%, H 7.94%, N 12.25%). It gives a single spot positive to ninhydrin at Rf 0.31 in the above-mentioned silica gel thin layer chromatography developed with the first-mentioned development solvent and at Rf 0.30 in the same thin layer chromatography developed with the second-mentioned development solvent. The molecular structure of these new kanamycin C derivatives has been identified by acid hydrolysis and by $^1H$ and $^{13}C$ nuclear magnetic resonance absorption spectra.

The minimum inhibitory concentrations (mcg/ml.) of 1-N-(L-4-amino-2-hydroxybutyryl)-kanamycin C (abbreviated as AHB-KC), 1-N-(L-4-amino-2-hydroxybutyryl)-3'-deoxykanamycin C (abbreviated as AHB-DKC) and 1-N-(L-4-amino-2-hydroxybutyryl)-3',4'-dideoxykanamycin C (abbreviated as AHB-DDKC) against various microorganisms were determined according to serial dilution method on nutrient agar medium at 37° C., the estimation being effected after 18 hours incubation. For comparison, the minimum inhibitory concentrations of 1-N-(L-4-amino-2-hydroxybutyryl)-kanamycin A (amikacin) was also determined in the same manner as described above.

The antibacterial spectra of these substances are shown in Table 1 below.

Table 1

| Test Organisms | Minimum Inhibitory Concentrations (mcg/ml.) | | | Amikacin (comparative) |
|---|---|---|---|---|
| | AHB-KC | AHB-DKC | AHB-DDKC | |
| Staphylococcus aureus FDA 209P | 6.25 | 6.25 | 12.5 | 0.39 |
| Mycobacterium smegmatis ATCC 607 | 3.13 | 12.5 | 6.25 | <0.20 |
| Escherichia coli NIHJ | 6.25 | 6.25 | 12.5 | 0.78 |
| Escherichia coli K-12 | 12.5 | 6.25 | 12.5 | 0.78 |
| Escherichia coli K-12 R5 | 6.25 | 6.25 | 12.5 | 0.39 |
| Escherichia coli K-12 ML 1629 | 6.25 | 6.25 | 6.25 | 0.78 |
| Escherichia coli K-12 ML 1630 | 12.5 | 12.5 | 12.5 | 0.78 |
| Escherichia coli K-12 ML 1410 | 25 | 6.25 | 25 | 0.78 |
| Escherichia coli K-12 ML 1410 R81 | 12.5 | 12.5 | 25 | 1.56 |
| Escherichia coli LA 290 R55 | 12.5 | 12.5 | 12.5 | 0.78 |
| Escherichia coli LA 290 R56 | 6.25 | 6.25 | 6.25 | 0.39 |
| Escherichia coli LA 290 R64 | 12.5 | 3.13 | 12.5 | 0.39 |
| Escherichia coli W 677 | 12.5 | 6.25 | 12.5 | <0.20 |
| Escherichia coli JR 66/W677 | 25 | 12.5 | 25 | 1.56 |
| Klebsiella pneumoniae PCI 602 | 3.13 | 3.13 | 6.25 | 0.39 |
| Klebsiella pneumoniae 22 No. 3038 | 12.5 | 6.25 | 25 | 1.56 |
| Pseudomonas aeruginosa A3 | 12.5 | 6.25 | 12.5 | 3.13 |
| Pseudomonas aeruginosa No. 12 | 50 | 50 | 100 | 3.13 |
| Pseudomonas aeruginosa TI-13 | 50 | 50 | 100 | 3.13 |
| Pseudomonas aeruginosa GN 315 | 50 | 50 | 100 | 100 |
| Pseudomonas aeruginosa 99 | 100 | 100 | 100 | 6.25 |
| Pseudomonas aeruginosa H 11 | 100 | 50 | 100 | 12.5 |

From the above Table, it is seen that the new compounds of this invention inhibit the growth of many kinds of bacterial strains. The new compounds of this invention further exhibit a extremely low acute toxicity to animals and men. It has been estimated that AHB-KC and AHB-DKC have an $LD_{50}$ value of more than 400 mg/kg upon intravenous injection in mice. Accordingly, the new compounds of the invention are promising as chemotherapeutic agents for therapeutic treatment of infections caused by gram-negative and gram-positive bacteria.

1-N-(L-4-Amino-2-hydroxybutyryl)-kanamycin A (amikacin) and 1-N-(L-4-amino-2-hydroxybutyryl)-kanamycin B are synthesized by Kawaguchi et al (U.S. Pat. No. 3,781,268), and these known compounds are acetylated by a 6'-acetyltransferase which is obtained from aminoglycoside-resistant strains, such as Pseudomonas aeruginosa GN315 (see, M. Yagisawa et al., J. Antibiot., 28, 486 (1975)) and in this respect they are in contrast with the new compounds of this invention which are not inactivated by the 6'-acetyltransferase.

The new compounds of the formula (I) according to this invention may readily be converted into the form of a pharmaceutically acceptable, nontoxic acid-addition salt such as the hydrochloride, sulfate, phosphate, nitrate, acetate, maleate, fumarate, succinate, tartarate, oxalate, citrate, ascorbate, methanesulfonate, ethanesulfonate and the like by reacting the free base form of 1-N-(L-4-amino-2-hydroxybutyryl) derivative of kanamycin C, 3'-deoxykanamycin C or 3',4'-dideoxykanamycin C with the appropriate acid in aqueous medium. The new kanamycin C compounds of this invention and their pharmaceutically acceptable acid-addition salt may be administered orally, intraperitoneally, intravenously, subcutaneously or intramuscularly using any pharmaceutical form known to the art for such administration and in a similar manner to the known kanamycins. For instance, the new compounds of this invention may be administered orally using any pharmaceutical form known to the art for oral administration. Examples of the pharmaceutical forms for oral administration are powders, capsules, tablets, syrup and the like. A suitable dose of the new compounds of this invention for effective treatment of bacterial infections is in a range of 0.5 to 4 g. per person a day when it given orally. It is preferred that said dose should be orally administered in three to four aliquots per day. The new compounds of this invention may also be administered by intramuscular injection at a dosage of 200 to 2000 mg per person two to four times per day. Moreover, the new compounds of this invention may be formulated into an ointment for external application which contains the active compound at a concentration of 0.5-5% by weight in mixture with a known ointment base such as polyethylene glycol. Furthermore, the new compounds of this invention are useful for sterilization of surgical instruments.

According to a second aspect of this invention, therefore, there is provided an antibacterial composition comprising as the active ingredient 1-N-(L-4-amino-2-hydroxybutyryl)-kanamycin C, 1-N-(L-4-amino-2-hydroxybutyryl)-3'-deoxykanamycin C or 1-N-(L-4-amino-2-hydroxybutyryl)-3',4'-dideoxykanamycin C or an acid-addition salt thereof in an antibacterially effective amount to inhibit the growth of bacteria, in combination with a carrier or vehicle for the active ingredient compound.

According to a further aspect of this invention, there is provided a process for the preparation of the 1-N-(L-4-amino-2-hydroxybutyryl) derivative of kanamycin C, 3'-deoxykanamycin C or 3',4'-dideoxykanamycin C represented by the general formula (I) shown hereinbefore, which comprises the steps of:

acylating the 1-amino group of kanamycin C, 3'-deoxykanamycin C or 3',4'-dideoxykanamycin C represented by the general formula (II):

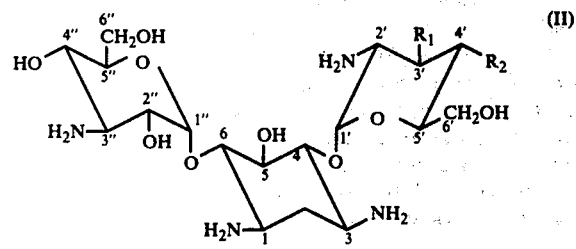

wherein $R_1$ and $R_2$ are each hydroxyl, or $R_1$ is hydrogen and $R_2$ is hydroxyl or $R_1$ and $R_2$ are each hydrogen or a nontoxic, pharmaceutically acceptable acid-addition salt thereof, by reaction with an amino-protected derivative of L-4-amino-2-hydroxybutyric acid or a functional equivalent thereof, to produce the 1-N-acylation product of the starting compound (II), and removing the amino-protecting group from the resulting 1-N-acylation product to give the compound of the formula (I).

The present process may include a further step of reacting the compound of the formula (I) so obtained, with a pharmaceutically acceptable acid to produce the corresponding pharmaceutically acceptable acid-addition salt of said compound of the formula (I), if desired.

In one embodiment of the process of this invention, the process may comprise the following steps of:

reacting the starting compound of the formula (II) of which amino groups are not protected, with an amino-protected derivative of L-4-amino-2-hydroxybutyric acid represented by the formula (III):

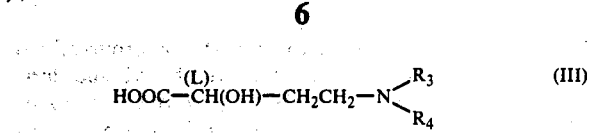

wherein $R_3$ is a hydrogen atom and $R_4$ is a known mono-valent amino-protecting group such as alkyloxycarbonyl, cycloalkyloxycarbonyl and aralkyloxycarbonyl, or $R_3$ and $R_4$ together form a divalent amino-protecting group such as phthaloyl group, or a Schiff base group (N=CHR$_5$ in which $R_5$ is a hydrogen atom, an alkyl group of 1-4 carbon atoms or an aryl group such as phenyl), in a manner known for the acylation of amino group, to produce the mixed acylation products comprising a 1-N-(L-4-protected-amino-2-hydroxybutyryl) derivative of the starting compound of the formula (II), treating the mixed acylation products in a known manner to remove the amino-protecting group therefrom, and then isolating the desired 1-N-(L-4-amino-2-hydroxybutyryl) derivative of the antibiotic according to the formula (I) by chromatographic separation of the acylation products from which the amino-protecting group has been removed, to recover the desired compound of the formula (I).

In carrying out the process of this invention, the starting kanamycin C, 3'-deoxykanamycin C or 3',4'-dideoxykanamycin C of the formula (II) of which amino groups are not protected, may be used either in the form of the free base or in the form of its acid-addition salt with an appropriate acid such as hydrochloric acid or sulfonic acid. In the acylation step of the present process, the reaction may be conducted generally as described in the specification of U.K. Pat. No. 1,426,908 or U.S. Pat. No. 4,001,208. Preferably, the starting compound of the formula (II) is dissolved in water and the resulting aqueous solution is adjusted to a pH of 6-8 and more conveniently at a pH of 6.5-7.0 by addition of an ordinary acid such as hydrochloric acid and sulfuric acid or an ordinary base such as aqueous sodium hydroxide and aqueous potassium hydroxide. To this solution of the above-mentioned partially protonated form of the starting compound is added a solution of an amino-protected derivative of L-4-amino-2-hydroxybutyric acid according to the formula (III) or a reactive derivative thereof which acts as a functional equivalent of the aforesaid amino-protected butyric acid derivative (III). In this way, the 1-amino group of the starting kanamycin C compound (II) is acylated with the acid (III).

The amino-protecting group available (for $R_3$ and/or $R_4$) in the amino-protected L-4-amino-2-hydroxybutyric acid derivative (III) employed in the acylation step of the present process may be a known amino-protecting group which is usually used in the conventional synthesis of peptides. However, the amino-protecting group employed must be such one of the nature which is removable readily by such a procedure and such reaction conditions which well not break or damage substantially the amido linkage present between the L-4-amino-2-hydroxybutyryl substituent and the 1-amino group of the aminoglycosidic moiety of the resulting acylation product when the removal of the amino-protecting group from the 1-N-aminoalkanoyl substituent of the acylation product is operated. Suitable examples of the mono-valent amino-protecting group which are available (as the group $R_4$) for the above purpose include an alkoxycarbonyl group of 2-6 carbon atoms such as tert-butoxycarbonyl and tert-amyloxycarbonyl; a cycloalkyloxycarbonyl group of 3-7 carbon atoms such as cyclohexyloxycarbonyl; an aralkyloxycarbonyl group such as benzyloxycarbonyl and p-methoxybenzyloxycarbonyl; and a substituted alkanoyl group of 2-5 carbon atoms such as trifluoroacetyl and o-nitrophenoxyacetyl. Preferred examples of the divalent amino-protecting group available (as the groups $R_3$ and $R_4$ taken together) for the above-mentioned purpose include phthaloyl group and a group of Schiff base type such as salicylidene. The introduction of the amino-protecting group into L-4-amino-2-hydroxybutyric acid may be achieved by reacting the latter with an appropriate reagent for the introduction of the amino-protecting group which is in the form of an acid halide, acid azide, active ester or acid anhydride, in the same manner as described e.g. in the specifications of U.S. Pat. Nos. 3,929,762 and 3,939,143 as well as the aforesaid U.K. Pat. No. 1,426,908.

The acylation of the 1-amino group of the starting kanamycin C compound of the formula (II) with the amino-protected L-4-amino-2-hydroxybutyric acid (III) may be conducted according to the conventional methods for the synthesis of amides using the acylating reagent (III) in the form of active ester such as N-hydroxysuccinimide ester, mixed acid anhydride or acid azide. As the starting kanamycin C compound (II) is insoluble or sparingly soluble in any organic solvent but soluble in water, it is preferred that the acylation reaction should be carried out in an aqueous reaction medium using the acylating agent (III) in the form of its active ester. For instance, a solution containing a 1-2 molar proportion of the N-hydroxysuccinimide ester of L-4-tert-butoxycarbonylamino-2-hydroxybutyric acid in a water-miscible organic solvent such as 1,2-dimethoxyethane and dimethylformamide may be admixed with an aqueous solution of 1 molar proportion of the starting kanamycin C compound (II) at a pH of 6-8 at ambient temperature under stirring to effect the desired acylation. The reaction temperature may be elevated, if desired. The reaction time may be for several hours and preferably for 5-6 hours.

The acylation product so obtained is, in fact, in the form of the mixed acylation products comprising the desired 1-N-(L-4-protected amino-2-hydroxybutyryl) derivative as well as the undesired, otherwise mono-N-acylated, di-N-acylated and poly-N-acylated products in which one or more of the 1-amino, 3-amino, 2'-amino and possibly 3''-amino groups of the kanamycin C moiety has or have been bonded with the L-4-protected amino-2-hydroxybutyryl substituent. The acylation product (the mixed acylation products) as such may be directly treated in the second step of the present process for the removal of the amino-protecting group, which is carried out in a manner known per se in the peptide synthesis. All of the amino-protecting groups of the above-mentioned nature may be removed readily by weak acid hydrolysis using an aqueous solution of trifluoroacetic acid or acetic acid or dilute hydrochloric acid. When the amino-protecting group is an aralkyloxycarbonyl group, the latter may be removed also by an ordinary hydrogenolysis.

The deprotected acylation product obtained from the second step of the present process is actually also in the form of the mixed products containing the desired 1-N-(L-4-amino-2-hydroxybutyryl)-kanamycin C, -3'-deoxykanamycin C or -3',4'-dideoxykanamycin C of the formula (I) and the undesired, otherwise acylated derivatives of the starting kanamycin C compound, together with the unreacted starting kanamycin C compound (II). In order to isolate the desired 1-N-acylation product (I) from the above mixed products, the latter may be subjected to a chromatographic separation method, such as ion-exchange chromatography using a cation-exchanger containing carboxylic functions, for example, Amberlite CG-50 (a product of Rohm & Haas Co., U.S.A.), CM-sephadex C-25 (a product of Pharmacia Co., Sweden) and carboxymethylcellulose; ion-exclusion chromatography using strong anion-exchange resin, for example, Dowex 1-X2 (a product of Dowex Co., U.S.A.); and column chromatography using silica gel. In this way, the isolation and recovery of the desired product (I) may be achieved with high efficiency. Particularly, it is recommendable that the deprotected mixed acylation product is chromatographed on Amberlite CG-50 (a weak cation-exchange resin containing carboxylic functions) using diluted aqueous ammonia as the development solvent, because this chromatographic procedure enables the desired product (I) as well as the unreacted starting kanamycin C compound (II) to be recovered efficiently and in pure state. According to these chromatographic methods, the desired kanamycin C derivatives of the formula (I) is usually recovered in the form of its free base, hydrate or carbonate.

"Sephadex LH-20" is a lyophilic insoluble molecular-sieve chromatographic medium made by cross-linking dextran and marketed by Pharmacia, Uppsala, Sweden. Sephedex LH-20 can be replaced by other similar gel-filtration agents, e.g. Sephadex G25 to G200, Sepharose 4B and 6B (Pharmacia Fine Chemicals AB, Uppsala, Sweden) and Bio-Gel A1.5 m (Bio Rad Co.). Preferred gel-filtration agents include the carboxymethyl substituted cross-linked dextran gels described in columns 3 and 4 of U.S. Pat. No. 3,819,836.

Dowex 1-X2(OH$^-$) is the basic or hydroxide form of cholestyramine resin which in its chloride form is a synthetic, strongly basic anion exchange resin containing quaternary ammonium functional groups which are attached to a styrene-divinylbenzene copolymer. Main constituent: Polystyrene trimethylbenzylammonium as Cl$^-$ anion, also contains divinylbenzene (about 2%) and water

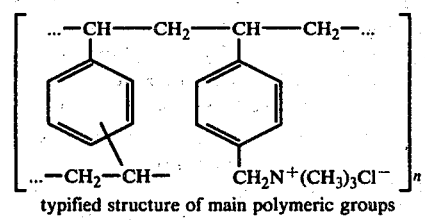

typified structure of main polymeric groups typified structure of main polymeric groups (about 43%). Cross linkage %: 1–10. Particle size: 50–100 mesh. Percent volume increase, new to exhausted (Cl$^-$ to OH$^-$) = 20%. Stable at temperatures up to 150°. Capacity: 3.5 meq/g dry, 1.33 meq/ml wet.

"Amberlite" is a registered trademark of the Rohm and Hass Company, Philadelphia, Pa. Amberlite IRC-50 and CG-50 are tradenames for weakly acidic cation exchange resins of a carboxylic-polymethacrylic type.

The invention is now illustrated with reference to the following Examples.

EXAMPLE 1

Synthesis of 1-N-(L-4-amino-2-hydroxybutyryl)-kanamycin C

A solution of 500 mg (1.02 millimole) of kanamycin C free base (hemihydrate) in 10 ml. of water was adjusted to pH 6.35 by addition of 3.2 ml. of 1N hydrochloric acid. To this solution was dropwise added over 5 minutes a solution of 500 mg (1.58 millimole) of N-hydroxysuccinimide ester of L-4-tert-butoxycarbonylamino-2-hydroxybutyric acid in 5 ml of dimethylformamide at ambient temperature under stirring. The admixture so obtained was stirred further for 6 hours to effect the acylation. The reaction solution comprising 1-N-(L-4-tert-butoxycarbonylamino-2-hydroxybutyryl)-kanamycin C so formed was concentrated to dryness under reduced pressure, and the solid residue was admixed with 16 ml of an aqueous solution of 90% trifluoroacetic acid. The mixture was agitated for 1 hour at ambient temperature to effect the removal of the amino-protecting tert-butoxycarbonyl group. The reaction solution was concentrated to dryness under reduced pressure and the residue was washed twice with 20 ml of ethylether to give 1.55 g of a colorless powder comprising a crude product of 1-N-(L-4-amino-2-hydroxybutyryl)-kanamycin C.

This crude product was taken up in 15 ml of water and the resulting solution was adjusted to pH 7.2 by addition of 1N aqueous ammonia and then passed through a column (inner diameter 20 mm) of 190 ml of Amberlite CG-50 (NH$_4$-form) for the adsorption of the desired product. After the column was washed with water (660 ml), it was eluted with 1940 ml of 0.1N aqueous ammonia and then with 1540 ml of 0.4N aqueous ammonia. The eluate was collected in 20 ml-fractions. The fractions Nos. 75–106 of the eluate obtained using 0.1N aqueous ammonia were combined together and concentrated to dryness under reduced pressure, recovering 199 mg of unreacted kanamycin C (recovery yield 40%). The fractions Nos. 152–175 of the eluate obtained using 0.4N aqueous ammonia were combined together and concentrated to dryness under reduced pressure to give 214 mg of a colorless powder containing the desired product. This powder was suspended in 2 ml of a mixed solvent of chloroform-methanol-17% aqueous ammonia (1:4:2 by volume), and the resulting suspension was passed through a column (inner diameter 14 mm) of 50 g of silica gel. The silica gel column was then developed with the above-mentioned mixed solvent, and the eluate was collected in 10 ml-fractions. The fractions Nos. 86–114 were combined together and concentrated to dryness under reduced pressure, and the residue was taken up into water. The resulting aqueous solution was chromatographed in a column of 5 ml of Amberlite CG-50 (NH$_4$-form) using 0.5N aqueous ammonia as eluent. The eluate was concentrated to dryness under reduced pressure, affording 49 mg of pure 1-N-(L-4-amino-2-hydroxybutyryl)-kanamycin C in the form of a colorless powder. Yield 8.0%. This powder had no definite melting point and decomposed at 167°–180° C. $[\alpha]_D^{26}$ +91% (c 1, water).

EXAMPLE 2

Synthesis of 1-N-(L-4-amino-2-hydroxybutyryl)-3'-deoxykanamycin C

A solution of 440 mg (0.92 millimole) of 3'-deoxykanamycin C free base (hemihydrate) in 8.8 ml of water was adjusted to pH 6.60 by addition of 2.75 ml of 1N hydrochloric acid. To this resulting solution was dropwise added over 10 minutes a solution of 449 mg (1.42 millimole) of N-hydroxysuccinimide ester of L-4-tert-butoxycarbonylamino-2-hydroxybutyric acid in 4.7 ml of dimethylformamide at ambient temperature under stirring. The admixture so obtained was stirred further for 6 hours at ambient temperature to effect the acylation. The reaction solution containing 1-N-(L-4-tert-butoxycarbonylamino-2-hydroxybutyryl)-3'-deoxykanamycin C so formed was concentrated to dryness under reduced pressure. The solid residue was admixed with 11 ml of an aqueous solution of 90% trifluoroacetic acid, and the mixture was agitated at ambient temperature for 1 hour to effect the removal of the amino-protecting tert-butoxycarbonyl group. The reaction solution was concentrated to dryness under reduced pressure and the residue was washed twice with 20 ml of ethylether to give 2.12 g of a crude product of 1-N-(L-4-amino-2-hydroxybutyryl)-3'-deoxykanamycin C as colorless powder.

This crude product was taken up into 15 ml of water, and the resultant aqueous solution was adjusted to pH 7.8 by addition of 1N aqueous ammonia and then passed through a column (inner diameter 20 mm) of 220 ml of Amberlite CG-50 (NH$_4$-form) to effect the adsorption of the desired product. After the column was washed with 1040 ml of water, it was eluted with 1340 ml of 0.2N aqueous ammonia and then with 1320 ml of 0.5N aqueous ammonia. The eluate was collected in 20 ml-fractions. The fractions Nos. 71–80 of the eluate obtained using 0.2N aqueous ammonia were combined together and concentrated to dryness under reduced pressure, recovering 149 mg of unreacted 3'-deoxykanamycin C (recovery yield 34%). The fractions Nos. 134–145 of the eluate obtained with 0.5N aqueous ammonia were combined together and concentrated to dryness under reduced pressure to give 155 mg of a colorless powder containing the desired product. This powder was suspended in 2 ml of a mixed solvent of chloroform-ethanol-17% aqueous ammonia (1:4:2 by volume), and the suspension so obtained was passed through a column (inner diameter 10 mm) of 25 g of silica gel, which was then developed with the above-mentioned mixed solvent. The effluent was collected in 3.2 ml-fractions. The combined fractions Nos. 99–140 were concentrated to dryness under reduced pressure, and the solid residue was taken up into water and chromatographed in a column of 5 ml of Amberlite CG-50 (NH$_4$-form) using 0.5N aqueous ammonia as the eluent. The eluate was concentrated to dryness under reduced pressure. Pure 1-N-(L-4-amino-2-hydroxybutyryl)-3'-deoxykanamycin C was obtained as a colorless powder. Yield 46 mg (8.5%). This powder had no definite melting point but decomposed at 151°–160° C. $[\alpha]_D^{27}$ +83° (c 1, water).

EXAMPLE 3

Synthesis of 1-N-(L-4-amino-2-hydroxybutyryl)-3',4'-dideoxykanamycin C

A solution of 340 mg (0.74 millimole) of 3',4'-dideoxykanamycin C free base (hemihydrate) in 7.5 ml of water was adjusted to pH 6.70 by addition of 2.45 ml of 1N hydrochloric acid. To this solution was dropwise added over 5 minutes a solution of 373 mg (1.18 millimole) of N-hydroxysuccinimide ester of L-4-tert-butoxycarbonylamino-2-hydroxybutyric acid in 3.75 ml of dimethylformamide at ambient temperature under stirring. The admixture so obtained was stirred further for 6 hours to effect the acylation. The reaction solution containing 1-N-(L-4-tert-butoxycarbonylamino-2-hydroxybutyryl)-3',4'-dideoxykanamycin C so formed was concentrated to dryness under reduced pressure, and the solid residue was admixed with 8.5 ml of an aqueous solution of 90% trifluoroacetic acid. The mixture was stirred for 1 hour at ambient temperature to effect the removal of the amino-protecting tert-butoxycarbonyl group. The reaction mixture was then concentrated to dryness under reduced pressure and the residue was washed twice with 20 ml of ethylether to give 1.46 g of a crude product of 1-N-(L-4-amino-2-hydroxybutyryl)-3',4'-dideoxykanamycin C as colorless powder.

This crude product was taken up into 14 ml of water and the resulting aqueous solution adjusted to pH 7.8 by addition of 1N aqueous ammonia. The solution was then passed through a column (inner diameter 20 mm) of 220 ml of Amberlite CG-50 (NH$_4$-form) for adsorption of the active compounds. After the column was washed with water (1040 ml), it was eluted with 1560 ml of 0.2N aqueous ammonia and then with 1460 ml of 0.5N aqueous ammonia so that the eluate was collected in 20 ml-fractions. The fractions Nos. 74-93 of the eluate obtained with 0.2N aqueous ammonia were combined together and concentrated to dryness under reduced pressure to recover 153 mg of unreacted 3',4'-dideoxykanamycin C (recovery yield 45%). The fractions Nos. 152-168 of the eluate obtained with 0.5N aqueous ammonia were combined together and concentrated to dryness under reduced pressure to give 116 mg of a colorless powder containing the desired product.

This powder was suspended in 2 ml of a mixed solvent of chloroform-ethanol-17% aqueous ammonia (1:4:2 by volume), and the resulting suspension was placed in a column (inner diameter 10 mm) of 25 g of silica gel, which was then eluted with the above-mentioned mixed solvent. The effluent was collected in 3.2 ml-fractions, and the fractions Nos. 71-96 were combined together and concentrated to dryness under reduced pressure. The residue was dissolved in water and the solution was chromatographed in a column of 5 ml of Amberlite CG-50 (NH$_4$-form) in the same manner as above using 0.5N aqueous ammonia as the eluent. The eluate was concentrated to dryness under reduced pressure to afford 35 mg of 1-N-(L-4-amino-2-hydroxybutyryl)-3',4'-dideoxykanamycin C as colorless powder. Yield 8.3%. This product showed no definite melting point but decomposed at 142°-158° C. $[\alpha]_D^{28}$ +76° (c 1, water).

EXAMPLE 4

The following tests were made to estimate how the pH of the reaction medium where the acylation reaction proceeded affected the yield of the desired acylation product 1-N-(L-4-amino-2-hydroxybutyryl)-kanamycin C.

Solutions each containing 50 mg (0.10 millimole) of kanamycin C free base (hemihydrate) in 0.5-1.0 ml of water were prepared and adjusted to different pH values by addition of varying volumes of 1N hydrochloric acid. To each solution was added dropwise a solution of 49 mg (0.15 millimole) of N-hydroxysuccinimide ester of L-4-tert-butoxycarbonylamino-2-hydroxybutyric acid at ambient temperature under stirring. The admixture so obtained was stirred for 6 hours to effect the acylation. The reaction solution was concentrated to dryness under reduced pressure and the solid residue was taken up into 1.2-1.4 ml of aqueous 90% trifluoroacetic acid. The resultant solution was stirred for 1 hour at ambient temperature, and the reaction solution was concentrated to dryness under reduced pressure. The residue was washed with ethylether to give a crude product. This crude product was chromatographed in the same manner as in Example 1 using a column (inner diameter 12 mm) of 20 ml of Amberlite CG-50 (NH$_4$-form), so that the unreacted kanamycin C was recovered in the pure state and a crude powder containing 1-N-(L-4-amino-2-hydroxybutyryl)-kanamycin C was obtained. The contents of 1-N-(L-4-amino-2-hydroxybutyryl)-kanamycin C in the crude powders so obtained were determined by measuring the antibacterial potency according to a standard cup-plate assay method using *Bacillus subtilis* PCI 219 as the test organism. In Table 2 below, there are shown the yield of unreacted kanamycin C recovered and the yield of the desired product formed, together with the pH value of the aqueous solution of the starting kanamycin C, the volume of water employed for the dissolution of the starting kanamycin C and the volume of the 1N hydrochloric acid added for the adjustment of the pH value.

Table 2

| pH | Volume of water (ml) | Volume of 1N HCl (ml) | Yield of kanamycin C recovered (%) | Yield of desired product formed (%) |
|---|---|---|---|---|
| 6.30 | 0.5 | 0.32 | 43 | 18 |
| 6.75 | 1.0 | 0.30 | 38 | 23 |
| 7.40 | 0.5 | 0.21 | 27 | 19 |
| 8.35 | 1.0 | 0.10 | 22 | 12 |

3'-Deoxykanamycin C and 3',4'-dideoxykanamycin C used in Examples 2 and 3 are new compounds which may be prepared by the following procedure (see co-pending British Patent Application No. 12266/77 and co-pending U.S. Patent Application Ser. No. 799,806): 3'-deoxykanamycin B or 3',4'-dideoxykanamycin B is reacted with tert-butyl chloroformate or tert-butyl S-4,6-dimethylpyrimid-2-ylthiocarbonate which is known as a reagent for introducing the amino-protecting tert-butoxycarbonyl group. In this way, there is prepared 6'-N-tert-butoxycarbonyl-3'-deoxykanamycin B or -3',4'-dideoxykanamycin B. The latter is then reacted with acetic anhydride to protect the 1,3,2' and 3''-amino group of the deoxykanamycin B compound with the another kind of the amino-protecting group, the acetyl group, whereby 6'-N-tert-butoxycarbonyl-tetra-N-acetyl-3'-deoxykanamycin B or -3',4'-dideoxykanamycin B is prepared. When this product is treated with aqueous 90% trifluoroacetic acid, the preferential removal of the tert-butoxycarbonyl group takes place, giving 1,3,2',3''-tetra-N-acetyl-3'-deoxykanamycin B or -3',4'-dideoxykanamycin B. 1,3,2',3''-Tetra-N-acetyl-3'-deoxykanamycin B or -3',4'-dideoxykanamycin B is dissolved in an aqueous acetic acid, and the resulting solution is treated with an aqueous sodium nitrite, when the 6'-amino group is converted into the 6'-hydroxyl group, giving 1,3,2',3''-tetra-N-acetyl-3'-deoxykanamycin C or -3',4'-dideoxykanamycin C. When the latter is treated for the removal of the amino-protecting acetyl groups, for example, by alkaline hydrolysis with 2N aqueous sodium hydroxide, there is produced 3'-deoxykanamycin C or 3',4'-dideoxykanamycin C.

The preparation of 3'-deoxykanamycin C or 3',4'-dideoxykanamycin C may be achieved in a similar way to the above-mentioned procedure by protecting the 6'-amino group of 3'-deoxykanamycin B or 3',4'-dideoxykanamycin B with benzyloxycarbonyl group. For this purpose, benzyloxycarbonyl chloride is employed as the reagent for introducing the amino-protecting benzyloxycarbonyl group. In this case, the removal of the benzyloxycarbonyl group from 6'-N-benzyloxycarbonyl-tetra-N-acetyl-3'-deoxykanamycin B or -3',4'-dideoxykanamycin B which is formed as the intermediate product may be conducted by conventional hydrogenolysis over palladium catalyst or platinum catalyst.

The preparation of 3'-deoxykanamycin C and 3',4'-dideoxykanamycin C is now illustrated below as Examples 5-6.

EXAMPLE 5

Synthesis of 3'-deoxykanamycin C (a) A solution of 2.0 g (4.3 millimole) of 3'-deoxykanamycin B in 40 ml of water was admixed with a solution of 1.03 g (4.7 millimole) of t-butyl S-4,6-dimethylpyrimid-2-ylthiocarbonate in 40 ml of dioxane, and the admixture so obtained was stirred for 24 hours at ambient temperature. The reaction mixture was then concentrated to dryness under reduced pressure, and the solid residue was taken up into 32 ml of water. The resultant aqueous solution was passed through a column of 160 ml of a cation-exchange resin, Amberlite CG-50 (ammonium form) for adsorption of the formed 6'-N-t-butoxycarbonyl-3'-deoxykanamycin B. The resin column was washed with 800 ml of water and then eluted with 800 ml of 0.1N aqueous ammonia. The eluate was collected in 15 ml-fractions, and the fraction Nos. 26 to 42 were combined together and concentrated to dryness under reduced pressure to give 1.06 g of a white colored powder comprising 6'-N-t-butoxycarbonyl-3'-deoxykanamycin B. Yield 44%. The resin column was further eluted with 0.5N aqueous ammonia to recover 452 mg of unreacted 3'-deoxykanamycin B.

(b) A solution of 211 mg (0.37 millimole) of 6'-N-t-butoxycarbonyl-3'-deoxykanamycin B in 5 ml of methanol was admixed with 2.5 ml of acetic anhydride, and the admixture was agitated for 5 hours at ambient temperature for the acetylation of the remaining amino groups. The reaction solution was admixed with a volume of water and then concentrated to dryness under reduced pressure to give a powder comprising 6'-N-t-butoxycarbonyl-tetra-N-acetyl-3'-deoxykanamycin B. Yield 296 mg.

(c) The product (235 mg) obtained in the preceding step (b) of this Example was dissolved in 2 ml of an aqueous solution of 90% trifluoroacetic acid and the resulting mixture was allowed to stand for 45 minutes at ambient temperature to effect the removal of the 6'-butoxycarbonyl group. The reaction mixture was concentrated to dryness under reduced pressure, and the solid residue obtained was washed with about 2 ml of ethyl ether to give 227 mg of a white colored powder comprising the tetra-N-acetyl derivative, that is, 1,3,2',3''-tetra-N-acetyl-3'-deoxykanamycin B.

(d) The powdery product (193 mg) obtained in the preceding step (c) of this Example was dissolved in 3.2 ml of an aqueous solution of 33% acetic acid, and to the resulting solution was added a solution of 265 mg of sodium nitrite in 3.2 ml of water and then 1.6 ml of acetic acid under ice-cooling and stirring. The mixture so obtained was stirred for 1 hour under ice-cooling and then for 16 hours at ambient temperature to effect the reaction where the 6'-amino group was converted into the 6'-hydroxyl group. The reaction solution was concentrated to dryness under reduced pressure to obtain 240 mg of a solid residue. This solid comprising 1,3,2',3''-tetra-N-acetyl-3'-deoxykanamycin C was taken up into 4 ml of 2N aqueous sodium hydroxide, and the resulting mixture was heated for 7 hours under reflux to effect the removal of the acetyl groups.

The reaction solution so obtained was admixed with 200 ml of water and then passed through a column (inner diameter 1.6 cm) of 50 ml of a cation-exchange resin, Amberlite CG-50 (70% ammonium form) for the absorption of the formed kanamycin C derivative. The resin column was washed with 250 ml of water and then eluted with 0.5N aqueous ammonia. The eluate was collected in 10 ml-fractions, and the fraction Nos. 58 and 59 were combined together and concentrated to dryness under reduced pressure to give 89 mg of a crude powder of 3'-deoxykanamycin C. This crude powder was taken up into 2 ml of water, and the aqueous solution obtained was again chromatographed using a column (inner diameter 0.75 cm) of 10 ml of Amberlite CG-50 (ammonium form) in such a manner that after washing with 30 ml of water, the resin column was eluted with 45 ml of 0.1N aqueous ammonia, and then with 45 ml of 0.2N aqueous ammonia. The eluate was collected in 1 ml-fraction, and the fraction Nos. 78 to 91 as combined together were concentrated to dryness under reduced pressure. A colorless purified powder of 3'-deoxykanamycin C (54 mg; 0.11 millimole) was obtained. Yield 45%.

EXAMPLE 6

Synthesis of 3',4'-dideoxykanamycin C (a) To a solution of 13.53 g (30 millimole) of 3',4'-dideoxykanamycin B in 135 ml of water was dropwise added over 1 hour 5.61 g (33 millimole) of benzyloxycarbonyl chloride under ice-cooling and stirring. After the dropwise addition was completed, the admixture so obtained was stirred for 1 hour at ambient temperature and the precipitate which formed was removed by filtration. The filtrate was washed with 135 ml of ethyl ether, and the aqueous layer was neutralized by addition of aqueous ammonia and then concentrated under reduced pressure. The concentrated solution so obtained was passed through a column of 480 ml of a cation-exchange resin, Amberlite CG-50 (ammonium form) for adsorption of the formed 6'-N-benzyloxycarbonyl-3',4'-dideoxykanamycin B. The resin column was washed with 1920 ml of water and then eluted with 0.1N aqueous ammonia. The first running (960 ml) of the eluate was discarded and the subsequent running (780 ml) was collected and concentrated to dryness under reduced pressure to give 5.43 g of a white colored powder comprising 6'-N-benzyloxycarbonyl-3',4'-dideoxykanamycin B. Yield 31%. The column was further eluted with 0.5N aqueous ammonia to recover 2.7 g of unreacted 3',4'-dideoxykanamycin B.

(b) 6'-N-Benzyloxycarbonyl-3',4'-dideoxykanamycin B (1.59 g; 2.72 millimole) was admixed with 160 ml of acetic anhydride and 16 g of sodium acetate, and the admixture so obtained was heated for 2 hours under reflux (at 110° C.) to effect the acetylation. The reaction mixture was concentrated to dryness under reduced pressure, and the solid residue was extracted with about 100 ml of acetone. The extract in acetone was concentrated to dryness under reduced pressure, leaving a solid (2.5 g). This solid was taken up into 10 ml of chloroform, and the resulting solution was passed through a column (inner diameter 2.6 cm) of 150 g of silica gel for adsorption of the formed acetylation product. The silica gel column was washed with 350 ml of chloroform and then eluted successively with 900 ml of chloroform-methanol (30:1 by volume), with 900 ml of chloroform-methanol (15:1 by volume) and with chloroform-methanol (10:1 by volume). The eluate was collected in about 14 ml-fractions. The fraction Nos. 91 to 149 as combined together were concentrated to dryness under reduced pressure to give 1.80 g of a white colored powder comprising 6'-N-benzyloxycarbonyl-tetra-N-acetyl-tetra-O-acetyl-3',4'-dideoxykanamycin B.

(c) The white colored powder (1.18 g) obtained in the above step (b) of this Example was dissolved in a mixture of 20 ml of methanol and 5 ml of water, and the resulting solution was subjected to catalytic reduction for 45 minutes under a stream of hydrogen over 1.61 g of 5% palladium-on barium carbonate added to said solution, so that the benzyloxycarbonyl group was removed. After removal of the catalyst by filtration, the reaction mixture was concentrated to dryness under reduced pressure, affording 942 mg of a white colored powder of the 6'-amino derivative, that is, 1,3,2',3"-tetra-N-cetyl-5,2",4",6"-tetra-O-acetyl-3',4'-dideoxykanamycin B.

(d) The white colored powder (942 mg) obtained in the above step (c) of this Example was dissolved in 16 ml of a solution of 33% acetic acid in water, and to the resulting solution were added 16 ml of a solution of 1.24 g of sodium nitrite and then 8 ml of acetic acid under ice-cooling and stirring. The admixture so obtained was stirred for 1 hour under ice-cooling end then for 3 hours at ambient temperature to effect the conversion of the 6'-amino group into 6'-hydroxyl group. The reaction mixture was concentrated to dryness under reduced pressure, and the solid residue was dissolved in 3 ml of chloroform. The solution in chloroform was passed through a column (inner diameter 2 cm) of 100 g of silica gel, which was then washed with 210 ml of chloroform and thereafter eluted successively with 660 ml of chloroform-methanol (50:1 by volume), with 1750 ml of chloroform-methanol (30:1 by volume), with 900 ml of chloroform-methanol (10:1 by volume) and with 700 ml of chloroform-methanol (5:1 by volume). The eluate was collected in about 14 ml-fractions. The fraction Nos. 220 to 270 as combined together were concentrated to dryness under reduced pressure, giving 587 mg of a white colored powder of tetra-N-acetyl-tetra-O-acetyl-3',4'-dideoxykanamycin C.

This white colored powder (234 mg) was taken up into 4 ml of 2N aqueous sodium hydroxide, and the resulting solution was heated for 7 hours under reflux to effect the removal of the acetyl groups. The reaction solution was dissolved in 200 ml of water and then passed through a column (inner diameter 1.6 cm) of 50 ml of a cation-exchange resin, Amberlite CG-50 (70% ammonium form) for adsorption of the desired product. After washing with 250 ml of water, the resin column was eluted with 0.5N aqueous ammonia to yield 122 mg of a crude powder of 3',4'-dideoxykanamycin C. A solution of this crude powder in 2 ml of water was passed through a column (inner diameter 0.8 cm) of 14 ml of Amberlite CG-50 ($NH_4$-form) for adsorption of the desired product. After washing with 45 ml of water, the resin column was eluted with 40 ml of 0.05N aqueous ammonia, then with 70 ml of 0.1N aqueous ammonia and finally with 70 ml of 0.2N aqueous ammonia. The eluate was collected in 1 ml-fractions, and the fractions Nos. 119 to 146 were combined together and concentrated to dryness under reduced pressure to give 90 mg of a colorless purified powder of 3',4'-dideoxykanamycin C. Overall yield 23%.

We claim:

1. 1-N-(L-4-amino-2-hydroxybutyryl)-3'-deoxykanamycin C or a nontoxic, pharmaceutically acceptable acid-addition salt thereof.

2. 1-N-(L-4-amino-2-hydroxybutyryl)-3'-deoxykanamycin C.

3. 1-N-(L-4-amino-2-hydroxybutyryl)-3',4'-dideoxykanamycin C or a nontoxic, pharmaceutically acceptable acid-addition salt thereof.

4. 1-N-(L-4-amino-2-hydroxybutyryl)-3',4'-dideoxykanamycin C.

* * * * *